US009259592B2

(12) United States Patent
Leijssen et al.

(10) Patent No.: US 9,259,592 B2
(45) Date of Patent: Feb. 16, 2016

(54) APPARATUS WITH WIRELESS COMMUNICATION MODULE

(75) Inventors: Jacobus Josephus Leijssen, Eindhoven (NL); Hubert Cecile Francois Martens, Eindhoven (NL); Michael Marcel Jose Decre, Eindhovn (NL); Jeroen Jacob Arnold Tol, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 735 days.

(21) Appl. No.: 13/119,038

(22) PCT Filed: Sep. 17, 2009

(86) PCT No.: PCT/IB2009/054052
§ 371 (c)(1),
(2), (4) Date: Mar. 15, 2011

(87) PCT Pub. No.: WO2010/035177
PCT Pub. Date: Apr. 1, 2010

(65) Prior Publication Data
US 2011/0175568 A1    Jul. 21, 2011

(30) Foreign Application Priority Data
Sep. 25, 2008   (EP) .................................... 08165071

(51) Int. Cl.
*H02J 7/00*       (2006.01)
*A61N 1/378*    (2006.01)
(Continued)

(52) U.S. Cl.
CPC .......... *A61N 1/3787* (2013.01); *A61N 1/36082* (2013.01); *A61N 1/37276* (2013.01); *A61N 1/00* (2013.01); *A61N 1/0529* (2013.01); *A61N 1/0534* (2013.01)

(58) Field of Classification Search
USPC ....................................... 320/108; 607/33, 61
See application file for complete search history.

(56) References Cited

U.S. PATENT DOCUMENTS

| 5,591,217 A | 1/1997 | Barreras |
| 5,769,877 A | 6/1998 | Barreras, Sr. |

(Continued)

FOREIGN PATENT DOCUMENTS

| CN | 201084137 Y | 7/2008 |
| JP | 2151134 A | 6/1990 |

(Continued)

OTHER PUBLICATIONS

Stengel, Bob "Efficiency Improvement for Battery Saver Sleep Mode" IP COM #IPCOM000006318D, Dec. 1, 1991. Motorola Inc. Technical Developments, vol. 14.

*Primary Examiner* — Samuel Berhanu

(57) ABSTRACT

The invention relates to an electronic apparatus (100) comprising a charging module (20) for receiving external energy (RF1) and for transferring it to a rechargeable energy storage (10) in a "charging state". Moreover, the apparatus comprises a processing module which can be operated in a working state that is enabled if the charging module (20) is in the charging state and the apparatus is in a standard operating mode. The processing module may for example be a communication module (30) that can communicate wirelessly in its working state. In the standard operating mode, communication with the apparatus (100) is thus only possible if the apparatus (100) is simultaneously charged. The communication module (30) can therefore be completely switched off during the residual time, thus reducing power consumption and avoiding erroneous communication or misuse.

13 Claims, 2 Drawing Sheets

(51) Int. Cl.
*A61N 1/36* (2006.01)
*A61N 1/372* (2006.01)
*A61N 1/00* (2006.01)
*A61N 1/05* (2006.01)

(56) References Cited

U.S. PATENT DOCUMENTS

| | | | |
|---|---|---|---|
| 5,807,397 A * | 9/1998 | Barreras | 607/61 |
| 6,005,489 A * | 12/1999 | Siegle et al. | 340/12.22 |
| 6,867,595 B2 * | 3/2005 | Chen | 324/433 |
| 6,894,456 B2 | 5/2005 | Tsukamoto | |
| 7,212,110 B1 | 5/2007 | Martin | |
| 2003/0045906 A1 * | 3/2003 | Stroebel et al. | 607/5 |
| 2004/0080299 A1 | 4/2004 | Forster | |
| 2004/0138713 A1 * | 7/2004 | Stickney et al. | 607/5 |
| 2005/0165317 A1 | 7/2005 | Turner | |
| 2005/0237025 A1 | 10/2005 | Osswald | |
| 2007/0060967 A1 | 3/2007 | Strother | |
| 2007/0145945 A1 * | 6/2007 | McGinley et al. | 320/114 |
| 2007/0293910 A1 | 12/2007 | Strother | |
| 2008/0046038 A1 | 2/2008 | Hill | |
| 2008/0132974 A1 | 6/2008 | Strother | |

FOREIGN PATENT DOCUMENTS

| | | |
|---|---|---|
| JP | 2000092571 A | 3/2000 |
| JP | 2005228194 A | 8/2005 |
| WO | 2008038202 A2 | 4/2008 |

* cited by examiner

APPARATUS WITH WIRELESS COMMUNICATION MODULE

FIELD OF THE INVENTION

The invention relates to an electronic apparatus, particularly an implantable active medial device like a Deep Brain Stimulation (DBS) device, comprising a rechargeable energy storage and a processing module, e.g. a wireless communication module. Moreover, it relates to a method for operating such an electronic apparatus and to an electronic system comprising such an electronic apparatus.

BACKGROUND OF THE INVENTION

Electronic devices with a rechargeable energy storage and with means for a wireless communication are known in a large variety of designs and for many different applications, for example as mobile computing devices, mobile phones, game consoles, remote controls etc. Important examples of such devices are also found in medical applications, for instance as implantable devices like the one described in the U.S. Pat. No. 6,894,456 B2, which is concerned with an implantable power module with means for inductive charging of a battery. Moreover, said power module comprises means for a remote communication via e.g. radiofrequency (RF). In this and similar devices, the radio communication means are always active, at least in a standby mode, which is associated with a continuous power consumption. Continuous power consumption by an RF-unit on stand-by is problematic in rechargeable implantable medical devices since the available energy is limited and the battery can only be recharged a limited number of times.

SUMMARY OF THE INVENTION

Based on this background it was an object of the present invention to provide means for realizing an improved operation of an electronic apparatus like an active implantable medical device, wherein it is particularly desirable that the power consumption is reduced and/or that the security of the system is increased.

This object is achieved by an electronic apparatus according to claim 1, a method according to claim 13, and an electronic system according to claim 14. Preferred embodiments are disclosed in the dependent claims.

According to its first aspect, the invention relates to an electronic apparatus, which may particularly (but not exclusively) be an implantable device like a Deep Brain Stimulation (DBS) device. The apparatus shall be operable in a "standard operating mode" which is defined in the following and which may in simple embodiments be the only possible operating mode of the apparatus. The electronic apparatus comprises the following components:

A rechargeable energy storage, typically realized by a battery or accumulator, though also other possibilities like (super-)capacitors may be possible.

A "charging module" that can assume a "charging state" in which it receives energy from outside the apparatus (called "external energy") via a "charging signal" and in which it can transfer all or some of the energy to the aforementioned energy storage. In most cases, the mentioned energy transfer to the storage will actually take place; it is however also comprised by the invention that in some cases the charging state is entered after reception of a charging signal without an ensuing energy transfer.

The charging module will typically comprise analogue and/or digital electronic hardware, and the energy transfer to the storage will typically be achieved by electrical currents. The external energy may be transferred to the charging module using e.g. inductive, capacitive, optical, or RF coupling.

A "processing module" that is adapted to fulfill some predetermined task in the apparatus, for example manage a communication, measure a physical quantity, process data/signals, or deliver electrical stimuli. The processing module can be operated in a "working state" which is, during the standard operating mode of the apparatus, only enabled if the charging state is assumed by the charging module. The "working state" is typically a state of special and/or increased activity or alertness of the processing module. The processing module will in many embodiments be completely inactive (switched off) when it is not in the working state. In other embodiments, the processing module may remain active to a certain degree after leaving the working state (e.g. in case of a pulse stimulation module in DBS).

It should be noted that in some embodiments of the apparatus there may be additional requirements (besides the existence of a charging state) that must be fulfilled before the working state of the processing module is actually entered (i.e. "enabling" the working state is not tantamount to actually entering it).

Moreover, the electronic apparatus may of course comprise several processing modules that may have different working states.

According to its second aspect, the invention relates to a method for operating an electronic apparatus that comprises an energy storage, a charging module, and a processing module, wherein said apparatus may particularly be an apparatus of the kind described above. The method comprises the following steps that are executed while the apparatus is in a "standard operating mode":

Making the charging module temporarily (transiently) assume a "charging state" in which it receives external energy and can transfer such energy to the energy storage.

Enabling a "working state" of the processing module only if the charging state is assumed.

The method comprises in general form the steps that can be executed with an electronic apparatus of the kind described above. Therefore, reference is made to the preceding description for more information on the details of that method.

According to the electronic apparatus and the method of the invention, there is a "standard operating mode" in which the processing module assumes its special "working state" at most simultaneously to an activity of the charging module. In other words, the working state is only possible during the standard operating mode while the apparatus receives a charging signal. This has the advantage that the processing module does not need to assume a standby mode in which it is continuously ready to enter the working state upon an external trigger signal; instead, it can be completely switched off, resulting in a zero power consumption outside the times the apparatus is recharged.

In the following, various further developments of the invention will be described that relate both to the electronic apparatus and the method described above.

A practically important case is realized when the processing module is or comprises a "communication module" that is adapted to provide in its working state for a wireless communication of an external device with the apparatus. The communication will typically take place by radiofrequency (RF) signals, though also other modalities like light or (ultra-)sound are conceivable. The communication with the communication module will apply usual protocols which may for example comprise handshaking procedures and/or encryption. It should be noted that in some embodiments of the apparatus there may be additional requirements (besides the existence of a charging state) that must be fulfilled for the communication module to enter its working state. An example of an additional requirement may be the presence of an embedded code in the charging signal that is received by the charging module.

In the standard operating mode of the apparatus, the aforementioned communication module can preferably be operated such that it is inactive outside its working state, i.e. if the charging module is not in its charging state. In this context, the "inactivity" of the communication module shall by definition comprise that it is impossible for an external device to start a communication with said module. The "activity" of the communication module, on the contrary, prevails in its working state and shall comprise both the execution of a communication as well as the mere readiness to start such a communication (e.g. if addressed by an external device), i.e. a standby-operation. Such a communication module will therefore become active only (i.e. at most) if the charging module is in its charging state. This has the advantage that the communication module can be completely switched off, resulting in a zero power consumption outside the times the apparatus is recharged. Moreover, the inactivity of the communication module outside charging times prevents that electromagnetic disturbances are erroneously interpreted as communication and that the communication can be misused by unauthorized persons ("hackers").

It was already mentioned that the charging module is preferably adapted to receive an RF charging signal. To this end, it will typically comprise an antenna, with which the energy of the electromagnetic waves is collected and converted into currents/voltages, and a receiver in which this energy is further processed (filtered, decoded with respect to a possible information contents, passed on to a battery, etc.). Similarly, the processing module will often comprise an antenna and a receiver, too, for example in the case of the above mentioned communication module. In a preferred embodiment of the invention, such an antenna and such a receiver of the charging module and/or the processing module can selectively be decoupled from each other during times of inactivity of the module. This decoupling prevents that energy from electromagnetic waves which can occasionally be captured by the antenna can enter the receiver, where it might damage sensitive electronic components. The decoupling in the charging module can for example be controlled by the processing module and vice versa.

Regarding the charging module, different possibilities for the reception of external energy are available. The external energy may for example be electrical energy transferred by wire (via a plug-in mechanism), light energy, thermal energy, chemical energy or the like. In a particularly important embodiment, the charging module comprises however an antenna for the wireless reception of radio-energy, i.e. of electromagnetic radio frequency (RF) waves (with a frequency of typically several MHz). A wireless energy transfer is particularly preferred in implantable devices to avoid problems with wired connections through the skin.

The charging module may assume its charging state, in which it receives energy and transfers (at least some of) this to the storage, based on some autonomous internal control (e.g. according to a fixed time schedule). Preferably, the charging module will however assume its charging state automatically when external energy is available for reception. As the charging process involves the uptake of a comparatively high power that needs no amplification, it will even be possible to initiate the charging state from a complete inactivity (switching off) of the charging module. In other words the external energy itself provides the power to wake up and operate the charging module for further reception and processing. Thus there is no necessity for a power consuming standby mode of the charging module. Both the charging module and the processing module can therefore be completely switched off most of the time, if the application at hand allows this.

In the aforementioned embodiment, the charging module may assume its charging state whenever it is reached by external energy. Alternatively, more elaborate procedures can be applied in which the charging module enters and/or leaves the charging state in dependence on a handshaking procedure (optionally combined with an asymmetric encryption code) with an external charging device. Thus the charging module can verify that a transfer of energy will start or has ended, respectively, which helps for example to ensure that the charging state is only assumed during an actual energy transfer (and not erroneously if e.g. electromagnetic noise has been captured). On the side of an external charging device, the handshaking procedure provides certainty that a known amount of energy has been transferred to the electronic apparatus in good order.

According to a further development of the invention, the charging module is adapted to detect a "working-state-enable" code or signal that has been transmitted from outside the apparatus, and the working state of the processing module is activated (provided the apparatus is in the standard operating mode) only if said "working-state-enable" code has been detected. The activity of the working state will therefore not automatically start whenever the charging module enters its charging state, but will additionally require that a "working-state-enable" code is received. This allows a more versatile operation of the electronic apparatus and extends the advantages of the inactivity of the processing module (e.g. power saving, avoidance of erroneous/improper/unintentional communication) to the times when recharging but no working state is desired. If for instance inductive coupling with varying magnetic fields at 100 kHz is used for charging, a code may be embedded in the 100 kHz signal using phase-shifting, frequency modulation, amplitude modulation or any other modulation technique known in the art. Alternatively, a code may be embedded in a different (higher) frequency signal that is added to the charging signal and that can be extracted out from the charging antenna of the charging module using filtering techniques. The charging antenna can consist of a loop or coil inside or outside the implant and this code can be extracted by appropriate circuitry in the implant connected to the loop/coil. Only if the appropriate code is detected the working state (e.g. a RF communication channel) may get enabled.

In a further development of the aforementioned embodiment, the "working-state-enable" code is individualized (unique) for the charging module. An external charging device that is able to transmit the "working-state-enable" code will therefore only be capable to activate communication in one particular electronic apparatus; if this charging device is for example stolen, it cannot be misused to initiate communication in other electronic apparatuses because its "working-state-enable" code will not be accepted by their charging modules.

In still a further development of the aforementioned embodiment, the "working-state-enable" code is additionally or alternatively individualized with respect to the session that is executed, i.e. it can be used to activate the working state only once (e.g. a communication in an electronic apparatus). Every new session, for example when a communication is interrupted or lost, requires a new, different "working-state-enable" code to activate the working state. This prevents that a "recorded" code, for example by eavesdropping, can falsely be used to start a process a second time.

As its name indicates, the "standard operating mode" will typically be the mode in which the apparatus is most of the time or perhaps even always. In an optional embodiment of the invention, there is at least one further mode which can be assumed by the apparatus. A preferred example of such an additional mode, which will be called "autonomous-operation mode" in the following, is characterized by the fact that the processing module is continuously or intermittently in its working state independent of the charging state. Communication with a communication module can then for example be initiated independently of a charging procedure. This may be desirable in exceptional situations, for example during implementation or removal of an implantable electronic apparatus, or if charging is not possible for some reason (e.g. a failure of the charging module) but communication shall nevertheless take place.

The switching from the "standard operating mode" to another mode, for example the aforementioned "autonomous-operation mode", may be initiated in various ways. The switching can for example be done via a communication with a communication module, or the "autonomous-operation mode" may automatically be started when some malfunction of the electronic apparatus is detected. According to a preferred embodiment, the charging module is adapted to detect a "mode-switching" code and to switch the apparatus from the "standard operating mode" into another mode (e.g. the "autonomous-operation mode") or vice versa upon detection of this code.

The handshaking procedures and the codes detected by the charging module, that were mentioned above in connection with various embodiments of the invention, are preferably embedded as a modulation into the flow of energy, i.e. the charging signal, that is transferred to the charging module. Thus the same receiving mechanisms can be used for both the energy transfer and for a (limited) communication with the charging module.

The "standard operating mode" as well as the mentioned possibility to send a "mode-switching" code to the charging module rely on an intact, working charging module. To reduce the risk that a vital function—for example a communication with the electronic apparatus—becomes impossible only because the charging module is defect, it is preferred that the processing module is adapted to interrupt the "standard operating mode" at predetermined times by periods of a "time-window operating mode" in which the working state (WS) is active. A person that knows the predetermined times can then for example use them to get in touch with a communication module irrespective of possible malfunctions of the charging module.

According to a further development of the invention, the processing module (e.g. the communication module and/or other components of the electronic apparatus) can consume more power in its working state than during the residual time. As external power is supplied to the electronic apparatus during the charging state (which is a prerequisite for the working state), more total power is available in the working state than during the residual times in which the energy storage is the only source of power. The processing module can exploit this extraordinarily high offer of power for tasks that are normally impossible, e.g. a high-power RF communication or low-noise measurements.

It was already mentioned that the electronic apparatus may serve many different purposes and accordingly may have many different designs. In a preferred embodiment, the processing module of the apparatus is adapted for generating electrical stimuli on external electrodes and/or for sampling sensor signals from external electrodes. Typically, the processing module will be supplied with energy from the energy storage (only). An example of such an apparatus is an implantable Deep Brain Stimulation (DBS) device that comprises electrodes for delivering stimuli to neural tissue in the brain and for sensing electrical activity of neurons.

The invention further relates to an electronic system comprising the following components:

An electronic apparatus of the kind described above with a rechargeable energy storage, a charging module, and a communication module, the apparatus having a "standard operating mode".

A charging device for energy transfer to the charging module of the electronic apparatus.

A communication device for communication with the communication module of the electronic apparatus.

Of course the charging device and the communication device have to be compatible to the electronic apparatus, i.e. they have to use the same modality (e.g. RF) and protocols for signal exchange.

BRIEF DESCRIPTION OF THE DRAWING

These and other aspects of the invention will be apparent from and elucidated with reference to the embodiment(s) described hereinafter. These embodiments will be described by way of example with the help of the accompanying drawings, in which.

DETAILED DESCRIPTION OF EMBODIMENTS

Though the invention will in the following be described with respect to an implantable device for Deep Brain Stimulation (DBS), it is not limited to this application. Instead, it can advantageously be applied in other medical implantable devices or in general in products that use particular functions like a wireless communication in which power consumption and/or safety is an issue. Particularly, the invention can be used in products in which radio communication and/or charging is a life supporting matter and/or extra safety is needed to switch on a radio communication and prevent unauthorized access (including damaging) to either the device.

Figure 1:
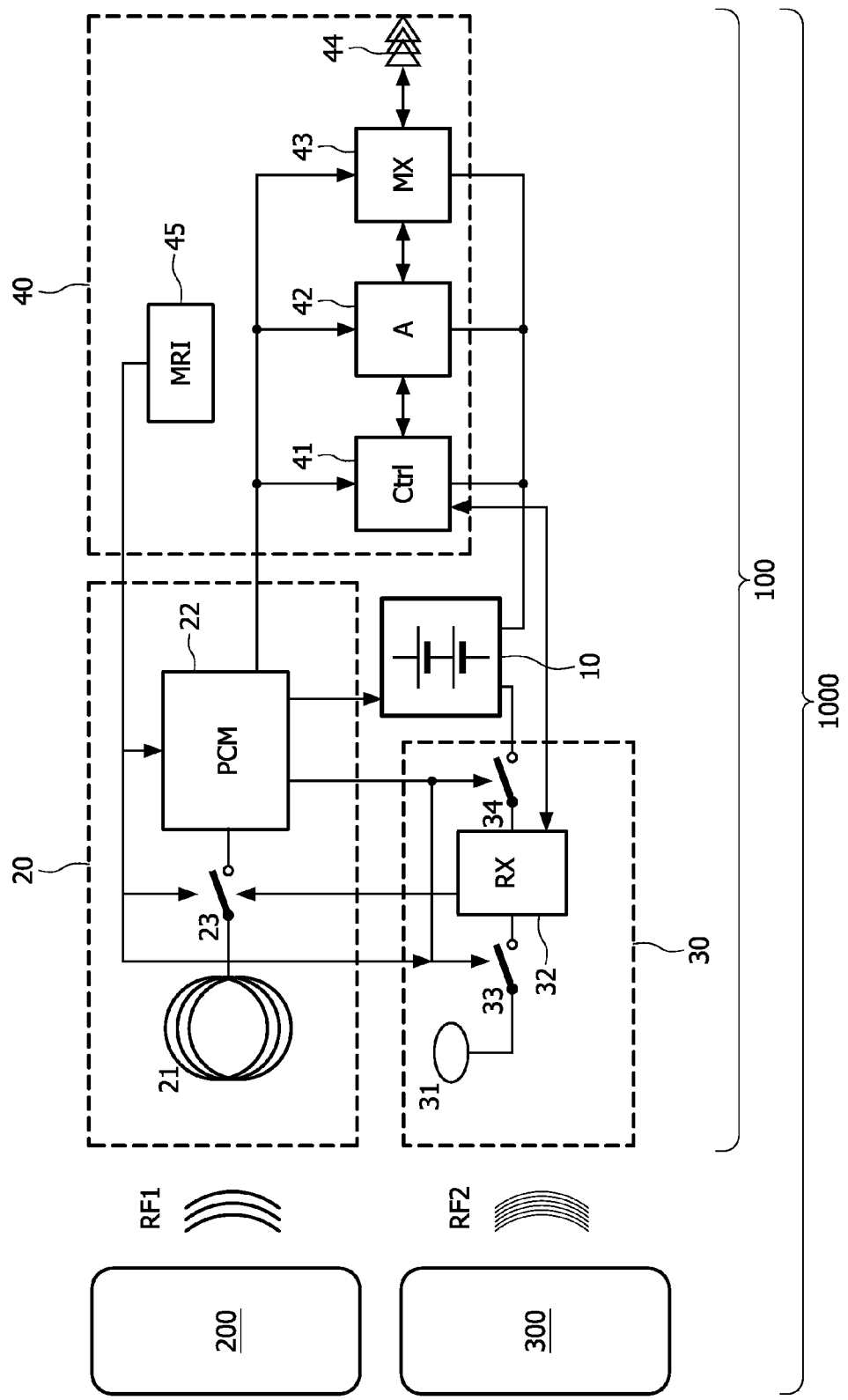
FIG. 1 schematically illustrates an electronic DBS apparatus according to the present invention.

FIG. 1 schematically illustrates a DBS system 1000 comprising an implantable DBS device 100, an external charging device 200, and an external communication device 300. Deep Brain Stimulation is a medical treatment methodology to apply electrical pulses to a certain brain area. This is usually done via an electrical probe consisting of stimulation contacts as well sensor contacts. DBS can for example be used for patients suffering the "Parkinson disease".

The implantable DBS device 100, which is typically arranged in a biocompatible casing (besides the electrodes 44), comprises the following components:

A rechargeable energy storage, realized for example by a rechargeable electrochemical battery 10. It should be noted that only schematic connections are indicated in the Figure and that for example connections to ground potential are omitted.

A charging module 20, comprising a charging coil 21 for absorbing external energy from external radio frequency (RF)

signals RF1 emitted by the external charging device 200, typically with a frequency of several MHz and with moderate power. Moreover, the charging module 20 comprises a Power/Charging Management unit 22 (abbreviated "PCM unit" in the following) that is coupled via a switch 23 to the coil 21. The PCM unit 22 is adapted to assume a "charging state" in which it collects the energy absorbed by the coil 21 and transfers it to the battery 10. Moreover, the PCM unit 22 is connected to other components of the DBS device 100 for control purposes.

A first "processing module" in the form of a communication module 30 for a wireless communication between the external communication device 300 and the DBS device 100. The communication module 30 comprises an antenna 31 for absorbing RF signals RF2 emitted by the external communication device 300, typically with a high frequency of e.g. hundreds of MHz and with low power. Moreover, it comprises a radio receiver 32 coupled to the antenna 31 for further processing (amplifying, decoding etc.) of the received signals and/or for generating signals that shall be emitted by the antenna as RF signals in a bidirectional communication.

A second "processing module" in the form of a working unit 40, comprising different components required for the essential task of the DBS device 100, namely a controller 41, an analogue unit 42 (e.g. an electrical pulse generator and/or a sensing unit for measurement of neural activity in the brains), and a multiplexer 43 to which different electrodes 44 are coupled (which are implanted into the brain). The enumerated modules 41, 42, 43 are coupled to the PCM unit 22 and the battery 10. Moreover, the controller 41 is bidirectionally coupled to the receiver 32.

The working unit 40 further optionally comprises a magnetic resonance imaging (MRI) unit 45 that is adapted to detect if the DBS device 100 is inserted into the magnetic field of an MRI system, which allows to switch it off for safety reasons. The MRI unit 45 may particularly be adapted to open the switches 23 and 33 (if an MRI field is detected) in order to prevent damage to the electronics caused by the induced voltages in the coil 21 and antenna 31, respectively, by the strong MRI fields.

A crucial aspect of the DBS device 100 is that there are control lines from the charging module 20 to the processing modules 30, 40. When the DBS apparatus 100 is in a "standard operation mode", these control lines can be used to enable a "working state" of the corresponding processing module 30, 40 only if the charging module 20 is in a charging state, i.e. if it receives external energy and transfers this to the battery 10.

A particularly important example of such a working state is the activity of the communication module 30. When the charging module 20 is not in its charging state (which will be the case for most of the time), the communication module 30 can completely be switched off, reducing its power consumption to zero. No further detection for switching on or off the communication module 30 is necessary. In contrast to this, the communication means of usual implantable DBS devices consumes power if communicating but also if switched to a standby or sleeping mode. The communication module 30 cannot be woken up by other signals, particularly not by disturbance signals captured by the antenna 31. The only possibility for a wake-up is that a charging current is flowing, i.e. that the charging state is assumed. Switching off the communication module 30 therefore also adds extra safety.

The described control of the communication module 30 can be achieved by a simple series switch element that is controlled by the PCM unit 22, e.g. a MOSFET 34 in the connection between the communication module 30 and its power supply 10.

Additionally a switch 33 (e.g. also a MOSFET) controlled by the PCM unit 22 can be inserted between the antenna 31 and the receiver 32. Opening this switch 33 prevents that energy randomly captured by the antenna 31 could damage sensitive electronic components (e.g. a low noise amplifier LNA) in the receiver 32 even in times this receiver 32 is switched off (by opening the MOSFET 34). This is also adds extra safety.

There are several possibilities to modify the described design of the DBS device 100 and to add more features. Thus it is for example possible to provide the energy-transferring charging signal RF1 with some information carrying code or modulation. In particular, a handshaking procedure can be provided between the external charging device 200 and the charging module 20. Thus the start and the ending of an energy transfer can securely be monitored. If the handshaking is combined with an asymmetric encryption code, it is possible to link the external charging device 200 uniquely to one individual implantable DBS device 100. In this case a stolen external charging device 200 cannot be misused for accessing other implanted DBS devices.

Besides the described "standard operation mode", in which the communication module 30 is at most active during the charging state of the charging module 20, further modes can be defined. Thus it may for example be advantageous to have an "autonomous-operation mode", in which the communication module 30 is continuously active (i.e. listening for external communication requests) or intermittently active with a more or less large duty cycle. The switching between the "standard operating mode" and another mode can for example be done via the detection of associated codes in the charging signal RF1 processed by the charging module 20.

Moreover, it may be possible for the processing modules of the DBS device 100 (e.g. the communication module 30 or the units 41-43 in the working unit 40) to execute a "high-power" operation during their working state, i.e. during the charging state of the charging module 20. During this "high-power" operation, more power than usually can be consumed by said components because not only the battery 10 but also the external power input RF1 are available. Thus it may for example become possible to improve the signal-to-noise ratio in sensing operations of the DBS device.

In another embodiment, the standard operation mode may be replaced by a "time-window operation mode", in which the working state is active irrespective of the charging state, during predetermined time windows which are known to the user (physician, patient). Thus the communication module 30 may for example be switched on by the PCM unit 22 during the predetermined time windows. Even if the communication channel via coil 21 is corrupted, it will then be possible to access the implanted device 100 during the predefined time windows.

As already mentioned, the connection between the coil 21 and the PCM unit 22 of the charging module 20 is protected by a switch 23 against an undesired and possibly harmful uptake of energy. The switch 23 can preferably be controlled by the communication module 30, in particular in such a way that it is opened if the DBS device 100 is in an autonomous-operation mode and/or time-window operation mode. This prevents that RF signals intended for the communication module 30 are (erroneously) processed by the PCM unit 22 or that charging signals not intended for the device or meant to damage it can have any effect.

According to a further development, the aforementioned opening of the switch 23 can be reversed at fixed times (e.g. via introduction of a "second time-window operation mode") to prevent that access to the DBS device 100 is lost in case of a failure of the communication module 30.

In summary, the proposed design of the DBS device 100 has the following advantages:

During normal use, the communication module 30 is not sensitive for disturbances in the medical implant frequency band or close to this frequency, because it is not powered. This extra safety for switching on the communication module 30 is particularly useful in view of the fact that the radio spectrum is getting more and more filled with signals.

No power consumption at all if no charging takes place, even not a very low one in idle modes etc.

No unexpected behavior of the communication module 30, even not if in an MR imaging machine.

In the most simple layout, only one series switching device is necessary, e.g. a MOSFET.

No misuse of the communication module 30, e.g. by hacker attacks, is possible outside the charging times.

Protection against an undesired processing of energy and/or information erroneously taken up by the antennas.

Figure 2:
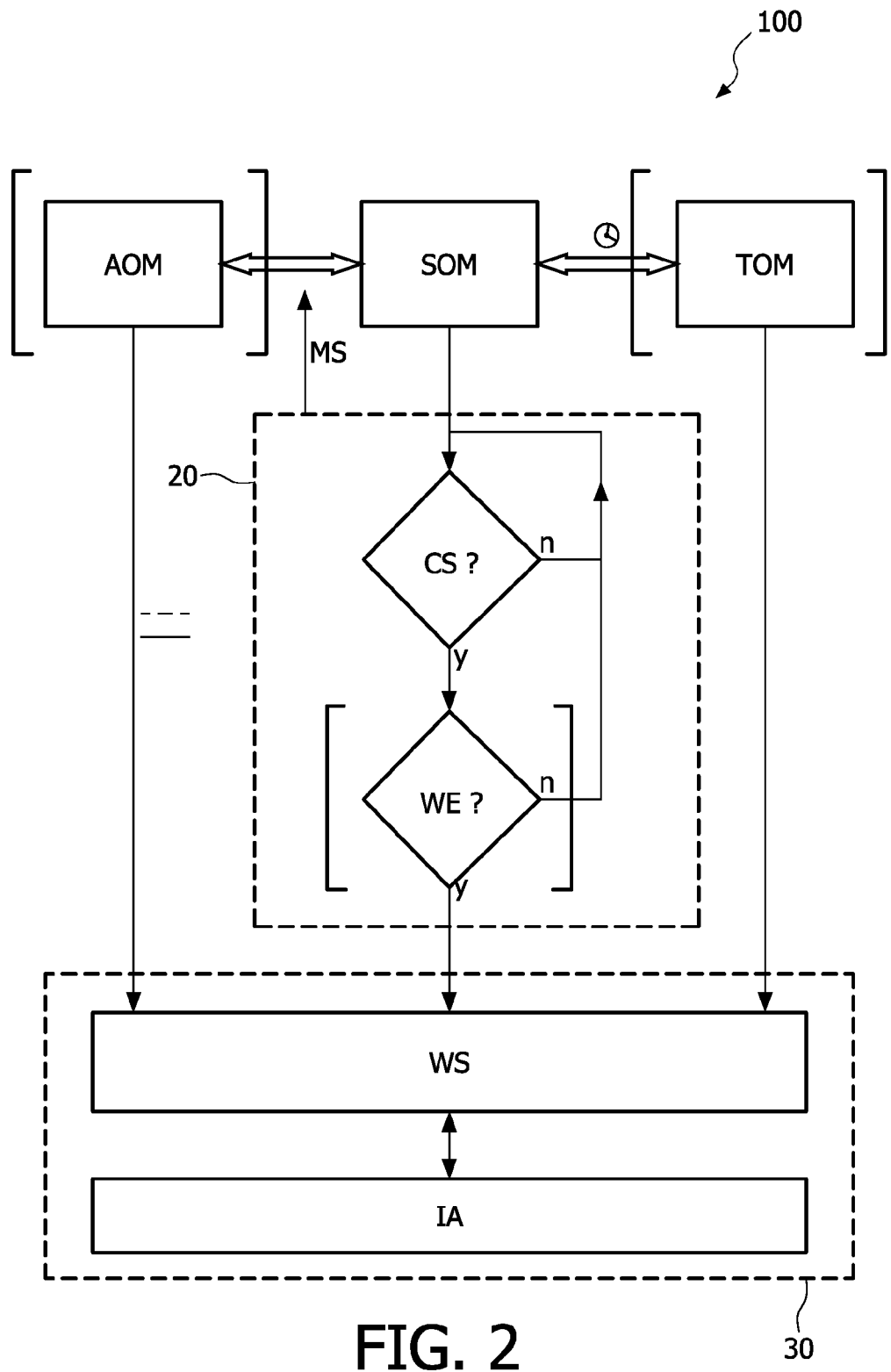
FIG. 2 is a flow chart illustrating the relations between the modes and states of the apparatus.

FIG. 2 illustrates the interaction of the different modes and states of an electronic apparatus 100 according to the present invention, wherein the following description is valid in general and not only for the DBS apparatus discussed in connection with FIG. 1.

The electronic apparatus 100 comprises a charging module 20 and a processing module 30, the latter being for example a communication module for a wireless communication. Furthermore, the apparatus 100 can be operated in a "standard operating mode" SOM, and the processing module 30 can enter a "working state" WS. The working state WS may for example correspond to an active RF communication. The state that is assumed alternatively to the working state WS may for instance be complete inactivity IA.

In the standard operating mode SOM of the apparatus 100, the working state WS of the processing module 30 is enabled only if the charging module 20 is in a "charging state" CS. Optionally, a start of the working state WS may additionally require that a "working-state-enable" code, WE, has been received by the charging module 20.

The apparatus 100 may optionally switch between the standard operating mode SOM and an "autonomous-operation mode" AOM, wherein the transition may be controlled by a "mode-switching" code MS received by the charging module 20. In the autonomous-operation mode AOM, the working state WS is continuously or intermittently assumed independent of the charging state of the charging module 20.

As another option the apparatus 100 may comprise a "time-window operating mode" TOM, which is entered during certain predetermined time windows and in which the working state WS is active irrespective of the state or activity of the charging module 20.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. An electronic apparatus that is operable in a standard operating mode (SOM), particularly a rechargeable active implantable medical device, the apparatus comprising:
   a rechargeable energy storage;
   a charging module configured to enter a charging state (CS) in which the charging module receives external energy (RF1) and is configured to transfer the external energy to the energy storage; and
   a processing module configured to process data, or deliver electric stimuli, or both, the processing module operable in a working state (WS) which is, while the apparatus is in the standard operating mode, only enabled if the charging state is entered.

2. The apparatus according to claim 1, wherein the processing module comprises a communication module that is adapted to communicate wirelessly in its working state (WS).

3. The apparatus according to claim 1, wherein the charging module, or the processing module, or both comprises an antenna and a receiver adapted to be selectively decoupled from each other in times of inactivity.

4. The apparatus according to claim 1, wherein the charging module enters the charging state (CS) when external energy is available.

5. The apparatus according to claim 1, wherein the charging module is adapted to enter the charging state, or to leave the charging state (CS), or both, in dependence on a handshaking procedure with an external charging device.

6. The apparatus according to claim 1, wherein the charging module is adapted to detect a working-state-enable (WE) code and that the working state (WS) is active during the standard operating mode (SOM) only if such a code has been detected.

7. The apparatus according to claim 6, wherein in that the working-state-enable (WE) code is individual for the charging module, or for a particular session, or both.

8. The apparatus according to claim 1, wherein the apparatus is adapted to enter an autonomous operation mode (AOM) in which the working state (WS) is continuously or intermittently active independent of the charging state (CS).

9. The apparatus according to claim 1, wherein the charging module is adapted to detect a mode-switching code (MS) and to switch the apparatus (100) from the standard operating mode (SOM) into another operating mode (AOM) or vice versa upon detection of the mode switching code (MS).

10. The apparatus according to claim 1, wherein the apparatus is adapted to interrupt the standard operating mode (SOM) at predetermined times by a time window operating mode (TOM) in which the working state (WS) is active.

11. The apparatus according to claim 1, wherein the processing module consumes more power during the working state (WS) than during a residual time.

12. The apparatus according to claim 1, wherein the processing module is adapted for generating electrical stimuli on, or for sensing sensor signals, or both, from external electrodes.

13. An electronic system, comprising:
   the electronic apparatus according to claim 2, comprising an energy storage, a charging module, and a communication module;
   a charging device for energy transfer to the charging module;
   a communication device for a wireless communication with the communication module.

* * * * *